United States Patent [19]

Lewis

[11] Patent Number: 4,660,408
[45] Date of Patent: Apr. 28, 1987

[54] PROPORTIONAL EXHAUST SAMPLER SYSTEM AND CONTROL MEANS

[75] Inventor: Gary W. Lewis, Fountain Valley, Calif.

[73] Assignee: Horiba Instruments Incorporated, Irvine, Calif.

[21] Appl. No.: 790,852

[22] Filed: Oct. 24, 1985

Related U.S. Application Data

[62] Division of Ser. No. 591,203, Mar. 19, 1984, Pat. No. 4,586,367.

[51] Int. Cl.$^4$ .................................................. G01M 15/00
[52] U.S. Cl. ........................................... 73/28; 73/863.12
[58] Field of Search ............. 73/28, 23, 863.12, 861.35

[56] References Cited

U.S. PATENT DOCUMENTS

| | | |
|---|---|---|
| 3,144,769 | 8/1964 | Francisco, Jr. .................. 73/861.35 |
| 3,407,646 | 10/1968 | Traver ..................................... 73/23 |
| 3,603,155 | 9/1971 | Morris et al. ....................... 73/863.1 |
| 3,699,814 | 10/1972 | Kaufman . |
| 3,965,749 | 6/1976 | Hadden et al. . |
| 3,986,386 | 10/1976 | Beltzer et al. ............................ 73/28 |
| 4,226,675 | 10/1980 | Lewis et al. ........................ 176/19 R |
| 4,351,181 | 9/1982 | Currans ................................... 73/23 |
| 4,379,402 | 4/1983 | Harman, III ............................ 73/23 |

Primary Examiner—Jerry W. Myracle
Attorney, Agent, or Firm—Harness, Dickey & Pierce

[57] ABSTRACT

A testing apparatus for measuring the particulate and-/or gaseous content of an exhaust source for use in evaluating the exhaust emissions of internal combustion engine provides both fixed flow and proportional flow control of the diluted particulate containing sample. The sample is diluted with carefully metered, clean dry air by means of one or more hybrid electrical-fluid control circuits for remarkably improved response time and accuracy.

4 Claims, 3 Drawing Figures

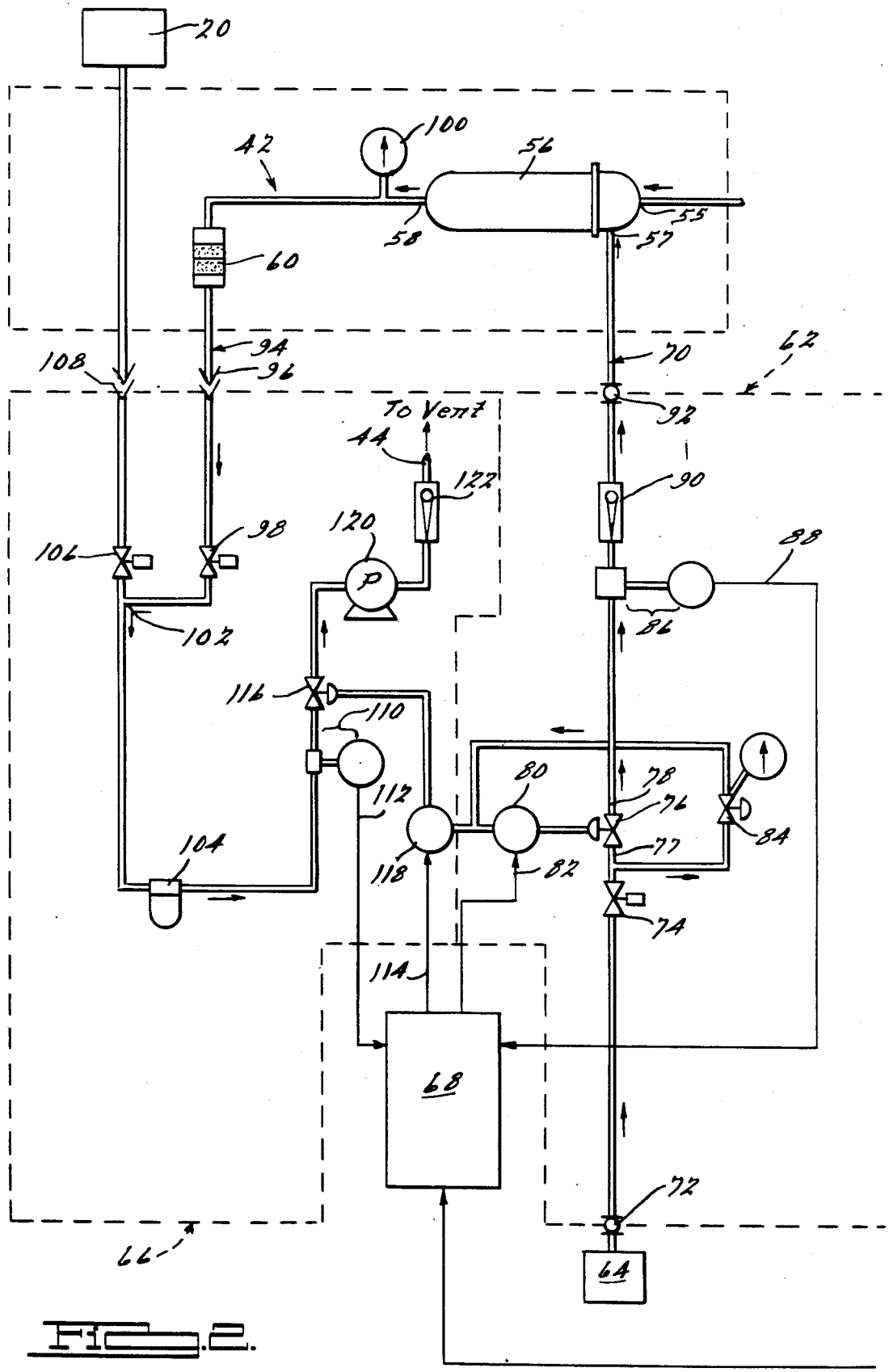

PROPORTIONAL EXHAUST SAMPLER SYSTEM AND CONTROL MEANS

This is a division of application Ser. No. 591,203, filed Mar. 19, 1984 now U.S. Pat. No. 4,586,367.

BACKGROUND OF THE INVENTION

1. Field of the Invention

This invention relates generally to equipment for measuring the exhaust emissions of internal combustion engines, and more particularly to an apparatus for measuring the particulate or gaseous content of exhaust emissions utilizing critical flow venturi metering system.

2. Description of the Prior Art

Under present day federal regulations the exhaust emissions from motor vehicles must not exceed specified values of certain contaminates. See Section 1201, Chapter XII, Title 45 of the Code of Federal Regulations, as published in the Federal Register, Vol. 36, No. 128, Friday, July 2, 1971, at pages 12652 et seq. See also Kaufman U.S. Pat. No. 3,699,814.

The presence of such standards has made it imperative that the exhaust emissions from vehicle engines be tested and analyzed to determine the relative amount of impurities therein. Much effort has gone into the development of equipment for use in this field of exhaust sampling, and it is not known to deliver exhaust gases from an internal combustion engine at an accurately controlled flow rate through a test apparatus for purposes of determining the analyzing the relative amounts of impurities. The general scheme of such testing is to add dilution air, in carefully controlled amounts, to the exhaust gases. The admission of dilution air cools the sample, making it easier to work with. The diluted sample is then distributed to various sample storage units for subsequent chemical analysis. Naturally the admission of dilution air must be in carefully controlled quantities in order for the test results to be repeatable and meaningful.

A system which satisfies these general requirements is described in the above identified portion of the Federal Register. However, the system described in the Federal Register suffers a number of difficulties and disadvantages, which are discussed in U.S. Pat. No. 3,699,814, to Kaufman, entitled "Gas Sampler", issued Oct. 24, 1972, and now assigned to the assignee of the present invention. The Kaufman patent, the disclosure of which is incorporated herein by reference, taught a much improved gaseous exhaust emissions sampler which replaced the troublesome constant displacement pump of prior systems with a critical flow venturi for metering the diltued exhaust emissions at a constant volume flow.

Initially, the analysis of motor vehicle exhaust emissions focused on the gaseous constituents, such as carbon monoxide and the oxides of nitrogen. However, with the increased popularity of diesel engines, present day exhaust emission analyzing equipment must now also be capable of measuring the hydrocarbon particulates of the exhaust emissions. Typically this is done by diverting a particulate containing sample through a filtration device, such as filter paper, for a predefined length of time, and then measuring the content of accumulated paticulate matter by weighing the filter paper.

For light duty diesel engines the particulate containing sample may be extracted directly from the mainstream diluted exhaust flow for accumulation on the filtration device. However, the procedure is not quite so simple for heavy duty diesel engines, due to the relatively high exhaust temperatures (nominally 350 degrees or higher). Accordingly, most present day exhaust emission measuring equipment employ a mixing duct where vehicle exhaust from the internal combustion engine under test is mixed with filtered dilution air. This lowers the temperature of the dilution sample. The diluted sample is then run through heat exchangers which further cool the sample and smooth out any temperature fluctuations which would otherwise alter the volumetric flow of the sample and destroy measurement accuracy. In order to accommodate heavy duty diesel engines and the higher exhaust temperatures produced by such engines, the above described equipment must be quite large to develop an adequate quantity of dilution air, and also require very large heat exchanging equipment and massive chillers for cooling the heat exchanging equipment. For example, in order to analyze the exhaust for a 500 cubic inch diesel engine, at a mainstream flow rate of 3000 cubic feet per minute, which may be considered typical in present day measuring equipment, a three ton heat exchanger measuring approximately 18 inches in diameter and about 5 feet in length would be required. In addition, the heat exchanger would require on the order of 50 ton refrigerated water chillers in order to maintain temperature requirements within Federal Register specifications. Naturally such systems are quite expensive and difficult to maintain.

One way of overcoming the problems associated with high temperature diesel exhaust is to use a double dilution system. Double dilution systems are known in which exhaust from the internal combustion engine under test is mixed with dilution air in a primary chamber or tunnel, and a sample from the primary tunnel is extracted and introduced into a secondary tunnel where additional dilution air is added. The double dilution system thereby provides a cooled, twice diluted sample which may then be analyzed for its pollutant content. Naturally, the double admission of dilution air must be carefully metered in order that the pollution content measurements will be repeatable and meaningful.

A common way of metering the admission of dilution air is through the use of constant flow systems which maintain the flow rate of both the mainstream flow within the primary tunnel and also the sample flow rate within the secondary tunnel to exacting tolerances. Maintaining constant flow conditions is not always easy to achieve. Fluctuations in temperature will directly affect the pressure-volume product of the gaseous constituents within the system, as provided by the physical gas laws. Hence, fluctuations in temperature will also affect the mass flow rates of the gaseous constituents and any suspended particulates. Therefore, in order to maintain mass flow rates constant it has heretofore been necessary to employ heat exchangers for maintaining a constant temperature of the gaseous and particulate constituents within the system. As noted earlier, these heat exchangers are quite large and require massive (and expensive) chillers for proper operation. It follows that heavy duty diesel engines which produce even hotter exhaust gases, will require even larger heat exchangers and chillers, hence the constant flow techique for metering the diluted exhaust test samples may be too expensive or otherwise undesirable for some testing facilities.

As an alternative to the constant flow techniques described above it has been recognized that the need for massive heat exchangers and chillers can be largely eliminated by using proportional sampling techniques. Using a proportional sampling technique, the flow within the system is monitored and flow controls are put in place to regulate the flow, or at least measure it so that the percentage of pollutant constituents can be scaled accordingly. While offering the considerable advantage of eliminating expensive heat exchangers and chilling equipment, prior art proportional control systems require expensive pumps, suffer from air leakage due to the relatively high operating pressures which the systems require, and are relatively sluggish or unresponsive to flow rate fluctuations of periods shorter than 10 seconds.

One prior art proportional sampling system uses a variable speed pump for creating the sample flow. The speed of the pump is controlled in accordance with an analog signal electronically derived from flow rate measurements. Another prior art system employs a control valve with built-in mass flow meter for regulating the flow within the system. Such flow control valves are quite flow restrictive and hence must be operated at relatively high pressures, in order to yield the desired flow rate. At such relatively high pressures commercially available pumps are quite leaky. Furthermore, because of the relatively high pressure requirements, the pumps cannot be used in a vacuum developing configuration, since vacuum operation is limited to vacuum pressures below 15 psi in relation to atmosphere. At the flow rates required a vacuum pressure of 15 psi is insufficient. Hence, there has heretofore been no way to place the leak prone pump in the fluid circuit where it will not affect the accuracy of the measurement system.

SUMMARY OF THE INVENTION

The present invention provides an apparatus for measuring the particulate and/or gaseous content of an exhaust source which may be used to evaluate the exhaust emissions of internal combustion engines, including light duty and heavy duty diesel engines. The invention overcomes the problems of prior art measurement systems and provides a system employing one or more mass flow meters disposed in a fluid circuit for operation at near optimal operating ranges, typically at near atmospheric pressures. The mass flow meters provide electrical signals which are processed through electronic compensation circuitry and differential amplifying circuitry to produce signals for controlling separate flow control valves. By separating the mass flow meters from the flow control valves, the performance of each component may be optimized and the electronic compensation circuitry can be easily tuned to provide faster response time and greater accuracy then can be had with prior art flow regulating devices. The invention further provides a fluid circuit whereby sample flow through the circuit is induced by a pump located in the fluid circuit after the mass flow meters and control valves. The pump is disposed in the circuit where any leakage caused by it will not affect the accuracy of the mass flow meter. Since pump leakage no longer affects accuracy, inexpensive pumps may be used in the present invention without degrading system performance.

The invention further provides for the admission of clean dry air to dilute the test sample. The use of dry air has the advantage of reducing the sample dew point to eliminate problems associated with moisture in mass flow measurement transducers.

Further in accordance with the invention, the sample flow through the fluid circuit may be established at a set point which is in turn established by one of at least two alternative mechanisms. The set point may be established by employing an analog voltage reference source which may be coupled to a differential amplifying circuit for comparing the measure flow rate (measured by the mass flow meters) to the desired set point. The comparison produces an error signal for controlling the flow control valve or valves in the circuit. This mechanism produces a fixed or constant dilution flow rate, such as might be used with heat exchangers for temperature stabilization. In the alternative, the invention provides a second mechanism for establishing the set point flow rate based on a varying or proportional rate for providing a linear dilution to sample ratio. In the proportional system the bulk stream flow rate is measured or computed based upon a measured bulk stream temperature and the calibration factor associated with the previously calibrated critical flow venturi. The calculation may be performed using a digital or analog computer appropriately coupled to the differential amplifying circuit for comparison with measured sample flow rates to produce an error signal for controlling the flow control valve or valves. The bulk stream flow rate is measured or calculated during system operation and is used to control the metering of the sample flow rate. The bulk stream need not be as closely temperature controlled, thus the heat exchangers and chillers can be eliminated. The invention further includes a switching means for selecting either the constant flow mechanism or the proportional flow mechanism. The ability to readily switch between these two mechanisms may be particularly beneficial in applications where a pre-existing installation already has heat exchanging equipment and is being upgraded to provide proportional sampling capabilities.

To summarize, the invention provides an apparatus for measuring the particulate and/or gaseous content of a source for use in a system having a sampling means for providing a particulate containing sample. The apparatus comprises a means for defining a flow confining path or fluid circuit which includes the sampling means and also includes a means for establishing a flow in the flow confining path. More specifically, the flow is established using a pump located downstream of the flow controlling mechanism and flow measuring mechanism. The invention further comprises a flow controlling means disposed in the flow confining path for providing a controlled pressure drop, thereby defining a first pressure side and a relatively lower second pressure side. A mass flow measuring device is coupled to respond to the second pressure side and provides a signal for controlling the flow controlling device.

The invention also provides an apparatus for measuring the particulate content of a source for use in a system having sampling means for providing a particulate containing sample and a fluid circuit communicating with the sampling means for establishing a flow of said sample. The invention further comprises a flow controlling means coupled with the fluid circuit for controlling the sample flow within the fluid circuit. A sensing means, coupled with the fluid circuit, provides a first electrical signal indicative of the sample flow within the fluid circuit. A transducing means is responsive to the first electrical signal and provides a fluid signal for controlling the flow controlling means. The fluid circuit comprises a first leg conducting at least a portion of the flow out from the sampling means and a second leg conducting at least a portion of the flow into the sampling means. Each leg is provided with a flow controlling means in accordance with the invention. More specifically, a first flow controlling means is coupled with the first leg and is responsive to a first sensing means coupled with the first leg for providing a signal indicative of sample flow within the first leg. The second leg is provided with a second flow controlling means which is responsive to a second sensing means coupled with the second leg for providing a signal indicative of the flow within the second leg. The second leg preferably conducts clean dry dilution air for discharge into the sampling means, while the first leg conducts the sample past a sampling device such as filter paper for extracting the particulate to be measured.

The invention further provides a particulate measuring means coupled to the sampling means for receiving the sample and measuring the particulates content thereof. A flow control means, coupled to the particulate measuring means, controls the receipt of the sample by the particulate measuring means. A pump is coupled to the flow controlled means and establishes a flow of the sample from the sampling means. The sampling means, the particulate measuring means, the flow control means, and the pump define at least a portion of a fluid circuit. The flow control means is disposed in the circuit between the sampling means and the pump.

For a more detailed understanding of the invention, its objects and advantages, references may be had to the following detailed description and to the accompanying drawings.

BRIEF DESCRIPTION OF THE DRAWINGS

FIG. 2 is a schematic flow diagram illustrating the invention; and

DESCRIPTION OF THE PREFERRED EMBODIMENT

Figure 1:
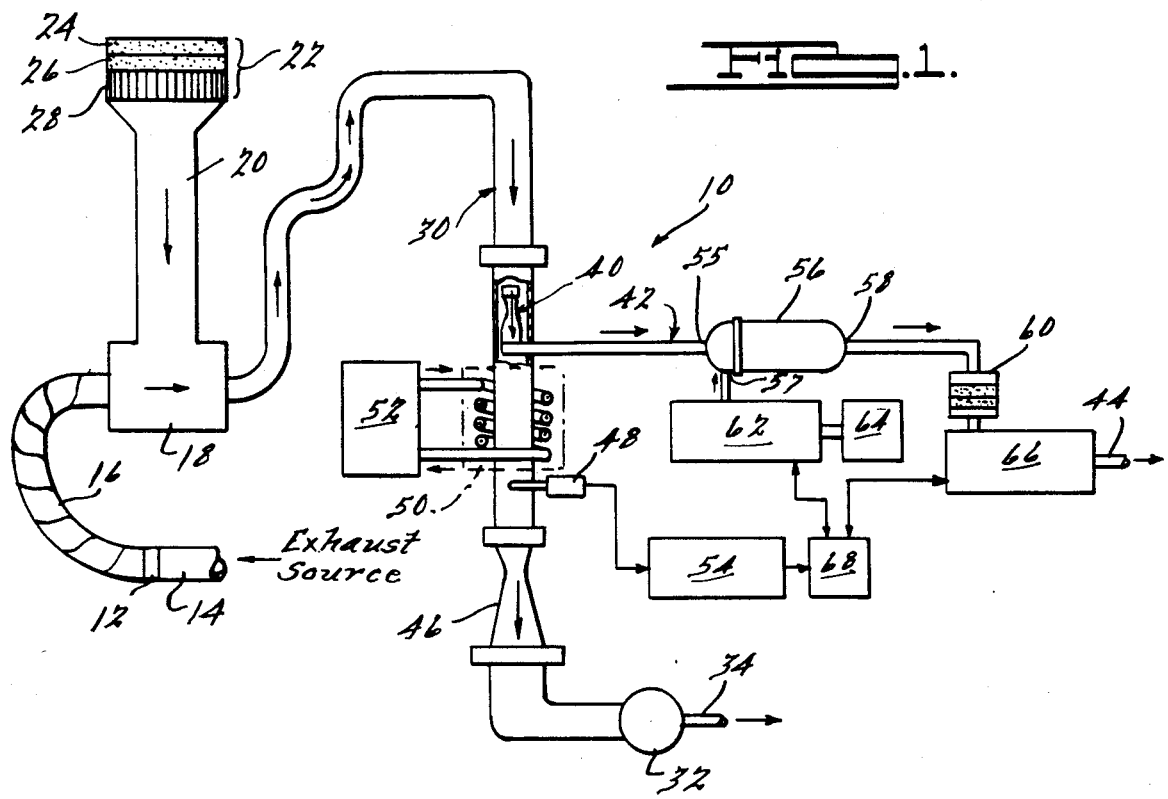
FIG. 1 is a diagrammatic illustration of an exhaust sampling system utilizing the present invention.

With reference to FIG. 1 a system for measuring the particulate content of a source is illustrated generally by reference numeral 10. The system comprises tailpipe adapter 12 for coupling to an internal combustion engine exhaust tailpipe 14. Exhaust from tailpipe 14 is introduced through exhaust inlet pipe 16 into mixing duct 18. Mixing duct 18 is coupled to air stack 20 which receives ambient inlet air through filter 22. Filter 22 may be implemented using a series of stacked filters such as pre-filter 24, charcoal filter 26 and absolute filter 28. Filter 22 serves generally to provide a supply of relatively pollution free inlet air which is mixed in mixing duct 18 with the exhaust from the exhaust source coupled to exhaust inlet pipe 16.

Mixing duct 18 is coupled in a primary fluid circuit designated generally by reference numeral 30 through which the mainstream exhaust/dilution air mixture flows. A centrifugal blower 32 is coupled in primary fluid circuit 30 and provides vacuum pressure to establish the mainstream flow. Blower 32 vents to atmosphere through discharge vent 34.

Coupled to fluid circuit 30 is a means for sampling the particulate containing bulkstream flow, referred to herein as sampling duct 40. Sampling duct 40 serves as a gas sample probe for extracting a sample from primary fluid circuit 30 and for providing the sample to a secondary fluid circuit 42. As will be more fully explained below, secondary fluid circuit 42 also vents to atmosphere as at discharge vent 44. Sampling duct 40 may also include temperature and static pressure probes (not shown).

A critical flow venturi provides the primary metering of the bulkstream flow through primary circuit 30. As explained fully in the Kaufman patent referenced above, critical flow venturi 46 is used to control and stabilize the bulkstream flow through circuit 30 and limits the flow in circuit 30, independent of the downstream vacuum, by virtue of sonic flow at its throat. Sonic, i.e., critical flow is maintained by producing a sufficient vacuum at the venturi exit by means of a centrifugal blower 32. Provided the temperature of the gases flowing through venturi 46 are known, the critical flow venturi may be used to establish a known flow rate. Temperature probe 48 is thus provided for measuring the gas temperatures immediately prior to entering critical flow venturi 46. In addition, a heat exchanger 50 coupled to chiller 52 may be provided for regulating the temperature of gases being input to the critical flow venturi, or for maintaining the gas temperatures within certain predefined limits. The critical flow venturi may be calibrated by measuring the critical flow rate at a given temperature. From this measured flow rate, other flow rates may be calculated, extrapolated, or derived from look-up tables in accordance with gas temperature at temperature probe 48. A digital or analog computer, such as computer 54, may be used to determine the bulkstream flow rate based upon the critical flow venturi calibration factor and measured temperature. While the critical flow venturi is presently preferred for establishing a continuous and well regulated bulkstream flow, the invention is not necessarily restricted to critical flow venturi systems, and would be equally usable in systems employing other types of controlled flow devices.

The particulate containing sample provided by sampling duct 40 is conveyed via secondary fluid circuit 42 to a first inlet 55 of secondary tunnel 56. A second inlet 57 to secondary tunnel 56 provides dilution air. The once diluted sample, extracted by sampling duct 40, is thus twice diluted in secondary tunnel 56 by the introduction of clean, dry air through second inlet 57. FIG. 1, therefore, illustrates a double dilution system. However, the invention is also usable in single dilution systems, and the employment of a secondary tunnel 56 for the admission of secondary dilution air is not to be construed as a limitation of the scope of the invention. Seconary tunnel 56 further includes outlet 58 which is coupled to filtration system 60, as part of fluid circuit 42. Filtration system 60 may be implemented using filter paper for trapping particulates during a predefined test period, for later weighing to determine the particulate content. In the alternative, a real time particulate measuring system may be employed to give a more immediate or direct indication of the particulate content passing through the secondary fluid circuit. In addition, the gaseous components may be routed through suitable conduits and collected in bags or receptacles for further laboratory analysis.

In accordance with the invention dilution air is introduced through second inlet 57 by means of dilution air metering device 62. Metering device 62 is receptive of clean dry air from a source 64 thereof. Also in accordance with the invention a sample metering device 66 is coupled to filtration system 60 for establishing and metering the flow of diluted sample from outlet 58 to discharge vent 44. Both metering devices 62 and 66 provide electrical signals to and receive electrical signals from an electronic particulate control unit 68. Electronic particulate control unit 68 also receives electrical signals from computer 54, if utilized. Metering devices 62 and 66 are illustrated in more detail in FIG. 2, while electronic particulate control unit 68 is illustrated in more detail in FIG. 3.

Referring now to FIG. 2, the dilution air metering device 62 and sample metering device 66 will now be discussed.

FIG. 2 illustrates secondary fluid circuit 42, as well as secondary tunnel 56, filtration system 60, electronic particulate control unit 68 and source of clean dry air 64. Dilution air metering device 62 is indicated generally within dashed box labeled 62 and sample metering device 66 is illustrated generally within dashed box 66. The dilution air metering device 62 will first be discussed by tracing the inlet leg 70 of secondary fluid circuit 42. Inlet leg 70 is coupled at one end to source of clean dry air 64, and at the opposite end to inlet 57 of secondary tunnel 56. Beginning at the source of clean dry air 64, inlet leg 70 proceeds through fitting 72 to a first solenoid valve 74 which is used to conserve clean dry air by shutting off leg 70 when the apparatus of the invention is not in use. In use, solenoid valve 74 is open. Next in the inlet leg circuit is flow control valve 76, which may be controlled to regulate or meter the flow of clean dry air through leg 70. Flow control valve 76 establishes a pressure drop between its inlet side 77 and is outlet side 78. Generally, the outlet side is at a lower pressure than the inlet side and flow is from source 64 to secondary tunnel 56, as indicated by the arrows on leg 70. Flow control valve 76 is actuated by current to pressure transducer 80. The current to pressure transducer is receptive of electrical signals via electrical lead 82 from particulate control unit 68 and provides fluid signals, i.e., pressure signals, for controlling the flow control valve. Current to pressure transducer 80 receives control air from pressure regulator 84, which is coupled to leg 70 upstream or at the inlet side of flow control valve 76. Pressure regulator 84 thus receives clean dry air, regulates it, and delivers it to the current to pressure transducer 80 where it is electrically modulated for controlling the flow control valve 76. Pressure regulator 84 is also the source of control air for other current to pressure transducers in the system, which are discussed below.

Downstream of the flow control valve is a mass flow meter device 86. The mass flow meter measures the mass flow rate through leg 70 of fluid circuit 42 and provides an electrical signal on lead 88 for coupling to the electronic particulate control unit 68. The electrical signal on lead 88 is indicative of the mass flow rate through leg 70 and is provided as a feedback signal to the control unit 68, where the signal is processed and delivered, via lead 82, for controlling the flow control valve 76. Thus, the feedback circuit in the air inlet leg will be seen as a hybrid fluid/electrical feedback signal. As will be explained in greater detail, the electronic particulate control unit 68 is capable of providing signal compensation to greatly improve the response time of the fluid/electrical hybrid system.

The circuit then proceeds through flow indicator 90 which provides a visual indication of the flow within leg 70. Leg 70 is then coupled through fitting 92 to the inlet 57 of secondary tunnel 56.

In practice, flow control valve 76 receives clean dry air at a pressure of nominally thirty pounds per square inch at a flow rate of approximately four cubic feet per minute and having a minus thirty degree Fahrenheit dew point. Flow control valve 76 drops the pressure to approximately one to two pounds per square inch on its outlet or downstream side 78. Hence, mass flow meter 86 is coupled in a fluid circuit at a pressure just slightly above atmospheric pressure. This greatly enhances the accuracy of the mass flow meter, since commercially available mass flow meters are most accurate at near atmospheric pressures and become increasingly less accurate as pressure increases. Furthermore, since a mass flow meter is employed, the flow measurement is relatively independent of pressure and temperature. By operating at or near atmospheric conditions the sensitivity to pressure and temperature is negligible.

Fluid circuit 42 includes an outlet leg 94 which is coupled generally between outlet 58 of secondary tunnel 56 and the discharge vent 44. Beginning at the secondary tunnel 56, outlet leg 94 proceeds through filtration device 60, discussed above, and through quick connect fitting 96 to solenoid valve 98. If desired a temperature sensor 100 may be coupled adjacent outlet 56 for measuring the temperature of the diluted exhaust sample. In a system receiving a particulate sample through inlet 55 at a temperature of 375 degrees, and also receiving clean dry air in a three to one air/sample ratio, the outlet diluted sample temperature is nominally less than 125 degrees. The fluid circuit proceeds through T-fitting 102 to a precautionary filter 104 which protects the sensitive downstream components from damage, should the system operator accidentally forget to install filter paper in the filtration system 60. Also coupled to T-fitting 102 is a normally open solenoid valve 106, which is coupled through quick-connect fitting 108 to a source of room air, such as airstack 20 of the primary fluid circuit 30, shown in FIG. 1. Solenoid valve 106 may be operated during calibration tests to measure the pollution content of the room air being used to dilute the exhaust source sample. In this way, any pollutants existing in the ambient air may be measured and accounted for, thereby increasing the accuracy of the particulate measurement.

From precautionary filter 104 the outlet leg 94 of fluid circuit 42 next encounters mass flow meter 110. Mass flow meter 110 is generally of the same type as mass flow meter 86. The mass flow meter 110, being coupled to secondary tunnel 56 is generally very near, or slightly below atmospheric pressure. Hence, mass flow meter 110 is relatively insensitive to pressure and temperature variations and is thus quite accurate. Mass flow meter 110 is coupled via electrical lead 112 to the electronic particulate control unit 68, and provides electrical signals to the control unit where they are processed and output on lead 114 for controlling a flow control valve 116. More specifically, lead 114 is coupled to a current to pressure transducer 118 which converts electrical signals from control unit 68 into fluid signals for controlling the flow control valve 116. Finally, leg 94 is coupled to pump 120 which provides vacuum pressures for developing a flow through leg 94. Pump 120 is coupled through flow meter 122, which provides a visual indication of the flow. Flow meter 122 is connected to discharge vent 44, thereby completing the outlet 94 of fluid circuit 42. It will be noted that pump 120 is downstream of mass flow meter 110, as well as flow control valve 116 and the filtration system 60. Hence, any leakage from pump 120 does not affect the flow rate through leg 94 or the measurements made by mass flow meter 110 and/or filtration system 60. This is a decided advantage since it permits the use of relatively inexpensive, and potentially leaky pumps. Pump 120 need only supply enough vacuum pressure so that flow control valve 116 can maintain the proper regulated flow. So long as pump 120 is capable of delivering adequate vacuum pressure, the accuracy of the pump is of no great concern. Fifteen pounds per square inch (15 psi) vacuum is adequate. It will also be noted that in both the inlet leg 70 and the outlet leg 94, the mass flow meters 86 and 110 are disposed in the respective fluid circuits so that they are separated from the flow producing pressure source by the flow control valves 76 and 116, respectively. In inlet leg 70, for example, the source of clean dry air 64 is pressurized to produce the flow, and mass flow meter 86 is disposed downstream of flow control valve 76. Thus, mass flow meter 86 is separated from the pressurized air source 64 by flow control valve 76. Similarly, in the outlet leg 94, pump 120 provides the vacuum pressure motive force and mass flow meter 110 is separated from pump 120 by flow control valve 116.

Figure 3:
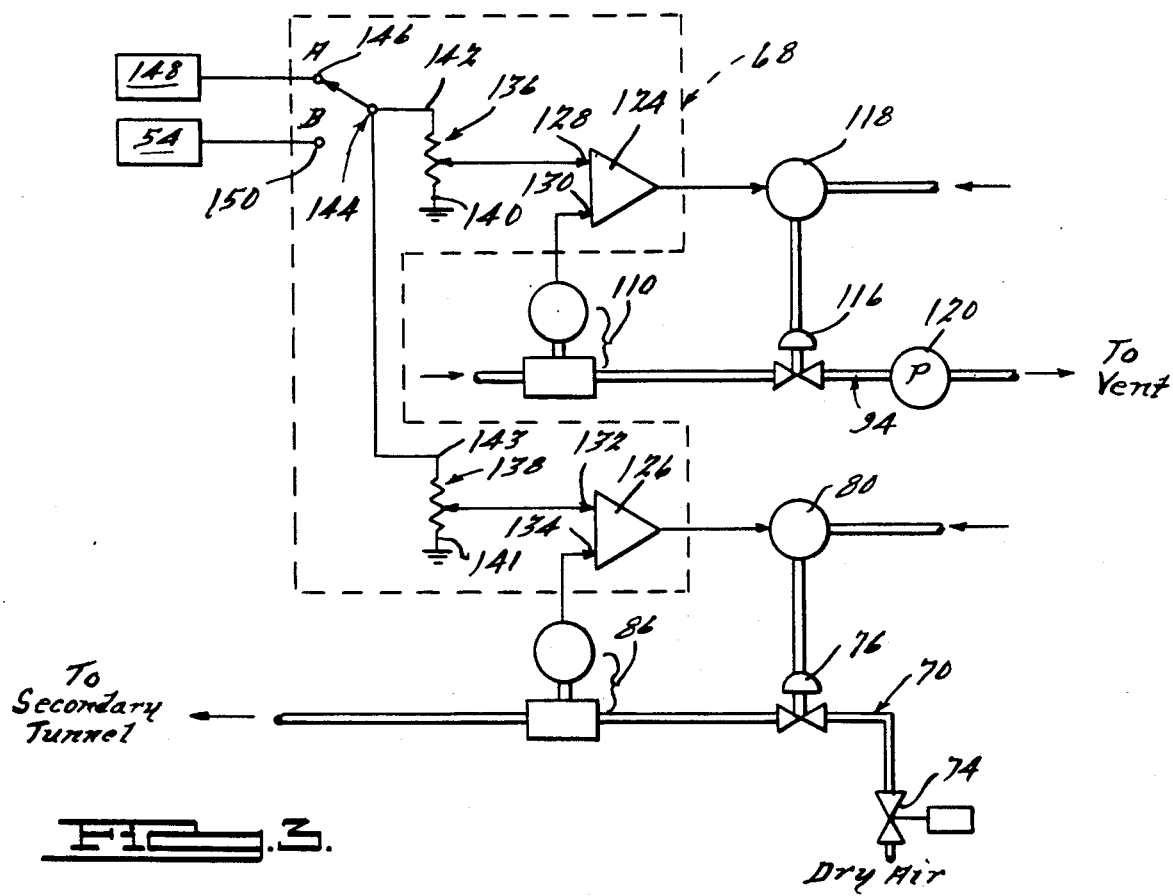
FIG. 3 is an electrical schematic diagram illustrating the electrical control unit of the invention in greater detail.

Referring now to FIG. 3, the electronic particulate control unit 68 will now be considered in greater detail. Control unit 68 comprises first differential amplifier 124 and second differential amplifier 126. Differential amplifier 124 provides electrical signals for controlling current to pressure transducer 118, while differential amplifier 126 provides an electrical output for controlling current to pressure transducer 80. Thus, differential amplifier 124 provides feedback control signals for regulating the flow in the outlet leg 94, and differential amplifier 126 provides similar feedback signals for regulating the flow in the inlet leg 70. Differential amplifier 124 has a first input 128 and a second input 130. Input 128 is coupled to a reference signal source, to be discussed below, and input 130 is coupled to mass flow meter 110, which provides an electrical signal indicating the measured mass flow. Differential amplifier 124 compares the reference signal at input 128 with the measured flow signal at input 130 and produces an error signal representing the deviation or difference between the actual measured flow rate and the reference or set point flow rate. This error signal is applied to current to pressure transducer 118.

Similarly, differential amplifier 126 includes a pair of input terminals 132 and 134. Terminal 132 is coupled to receive a reference signal from a reference source, yet to be discussed, while terminal 134 is coupled to mass flow meter 86 which provides a signal indicative of the measured mass flow rate. Differential amplifier 126 compares the signals at input terminals 132 and 134 and produces an error signal indicative of the deviation or difference between the two input signals. This error signal is applied to current to pressure transducer 80, which in turn controls flow control valve 76.

The reference signals coupled to input terminals 128 and 132 are analog signals derived from voltage divider potentiometers 136 and 138. Preferably, potentiometers 136 and 138 are ten turn potentiometers. Potentiometer 136 provides the reference signal to differential amplifier 124, and potentiometer 138 provides the reference signal to differential amplifer 126. Preferably, both potentiometers 136 and 138 have a first terminal 140 and 141, respectively, coupled to ground and second terminals 142 and 143, respectively, coupled to single pole double throw switch 144 or the electronic equivalent thereof. Switch 144 has a first terminal 146 which is coupled to an analog reference voltage source 148. Reference source 148 may be implemented using a battery or direct current power supply. Switch 144 includes a second terminal 150 which is coupled via the appropriate linkage to computer 54. It will be recalled that computer 54 is responsive to the temperature in the primary circuit and provides a signal indicative of the bulkstream mass flow in the primary circuit. When switch 144 is in the A position (as illustrated in FIG. 3), both differential amplifiers 124 and 126 are provided with a constant analog reference signal. Thus, the output error signals of these amplifiers produce a constant flow rate in the secondary circuit. When switch 144 is thrown to the B position, the differential amplifiers 124 and 126 receive a proportional reference signal from computer 54. Thus, the error signals produced by these amplifiers cause a proportional flow in the secondary circuit. One benefit of the proportional flow operation is that it allows the system to automatically compensate for changes in temperature, hence it eliminates the need for heat exchangers. Switch 144 thus provides a convenient means for switching from a constant flow configuraiton to a proportional configuration. This highly desirable feature permits the invention to be installed in existing testing facilities which already have heat exchangers and may wish to continue using those heat exchangers for certain measurements.

While it will be apparent that the preferred embodiment of the invention disclosed is well calculated to fulfill the objects stated above, it will be appreciated that the invention is susceptible to modification, variation and change without departing from the proper scope or fair meaning of the invention, as defined by the following claims.

I claim:

1. An apparatus for measuring the particulate content of a source for use in a system having sampling means for providing a particulate containing sample comprising:
   a valve having an inlet for coupling to a pressurized source of substantially dry dilution air and having an outlet communicating with said sampling means for adding said dilution air to said sample;
   a mass flow meter operably coupled between said outlet and said sampling means for producing a flow signal in response to the mass flow of said dilution air; and
   control means coupled to said valve and said mass flow meter for operating said valve in response to said flow signal to add a metered quantity of dilution air to said sample.

2. The apparatus of claim 1 wherein said mass flow meter is coupled to measure said flow at substantially atmospheric pressure.

3. The apparatus of claim 1 wherein said flow signal is an electrical signal and said control means comprises differential amplifier receptive of said flow signal and receptive of a reference signal indicative of desired dilution air mass flow.

4. The apparatus of claim 1 wherein said control means is responsive to signals from a computer.

* * * * *